US012649024B2

(12) United States Patent
Penka et al.

(10) Patent No.: US 12,649,024 B2
(45) Date of Patent: Jun. 9, 2026

(54) DYNAMIC CONTROL OF SUBORDINATE PUMPS IN A HEART-LUNG-MACHINE

(71) Applicant: LivaNova Deutschland GmbH, Munich (DE)

(72) Inventors: Ottmar Penka, Munich (DE); Friedemann Schubert, Munich (DE)

(73) Assignee: LivaNova Deutschland GmbH, Munich (DE)

( * ) Notice: Subject to any disclaimer, the term of this patent is extended or adjusted under 35 U.S.C. 154(b) by 947 days.

(21) Appl. No.: 17/846,354

(22) Filed: Jun. 22, 2022

(65) Prior Publication Data

US 2023/0023854 A1       Jan. 26, 2023

Related U.S. Application Data

(60) Provisional application No. 63/224,224, filed on Jul. 21, 2021.

(51) Int. Cl.
A61M 1/36 (2006.01)
A61M 1/16 (2006.01)

(52) U.S. Cl.
CPC ........ A61M 1/3666 (2013.01); A61M 1/1698 (2013.01); A61M 1/3632 (2014.02); A61M 1/3624 (2013.01); A61M 2205/3334 (2013.01)

(58) Field of Classification Search
CPC .............. A61M 1/1698; A61M 1/3607; A61M 1/3624; A61M 1/3632; A61M 1/3666; A61M 2205/3334
See application file for complete search history.

(56) References Cited

U.S. PATENT DOCUMENTS

| | | | |
|---|---|---|---|
| 4,540,399 A | 9/1985 | Litzie et al. | |
| 5,820,579 A | 10/1998 | Plotkin | |
| 6,974,434 B2 | 12/2005 | Roberts et al. | |
| 7,022,099 B2 | 4/2006 | Litzie et al. | |
| 8,690,784 B2 | 4/2014 | Ranucci | |
| 9,393,357 B2 | 7/2016 | Ellingboe et al. | |
| 9,452,250 B2 | 9/2016 | Penka et al. | |
| 2006/0089586 A1 | 4/2006 | Kaus et al. | |
| 2007/0073097 A1 | 3/2007 | Borra et al. | |
| 2007/0073393 A1* | 3/2007 | Kung .................. | A61M 60/196 417/43 |

(Continued)

FOREIGN PATENT DOCUMENTS

| | | |
|---|---|---|
| WO | 2020125976 A1 | 6/2020 |
| WO | 2020126007 A1 | 6/2020 |

(Continued)

*Primary Examiner* — Jennifer Wecker
*Assistant Examiner* — Jonathan Bortoli
(74) *Attorney, Agent, or Firm* — Seager, Tufte & Wickhem LLP

(57) ABSTRACT

Methods and systems for controlling one or more pumps of a heart-lung-machine. An illustrative method may comprise receiving an actual flow rate of a pump, determining the actual flow rate is from a primary pump, determining an available amount of the actual flow rate of the primary pump that is available to one or more subordinate pumps, comparing the available amount of the actual flow rate of the primary pump to a sum of set flow rates of the one or more subordinate pumps, and operating the one or more subordinate pumps in a proactive control mode or a reactive control mode.

5 Claims, 3 Drawing Sheets

(56) References Cited

U.S. PATENT DOCUMENTS

| | | | | |
|---|---|---|---|---|
| 2010/0168639 A1* | 7/2010 | Cantu | ................ | A61M 1/3441 |
| | | | | 604/4.01 |
| 2018/0250464 A1 | 9/2018 | Turner | | |

FOREIGN PATENT DOCUMENTS

| | | | |
|---|---|---|---|
| WO | 2020126008 A1 | 6/2020 | |
| WO | 2020136652 A1 | 7/2020 | |
| WO | 2020259837 A1 | 12/2020 | |

* cited by examiner

DYNAMIC CONTROL OF SUBORDINATE PUMPS IN A HEART-LUNG-MACHINE

CROSS REFERENCE TO RELATED APPLICATIONS

This application claims the benefit of U.S. Provisional Patent Application Ser. No. 63/224,224 filed on Jul. 21, 2021, the disclosure of which is incorporated herein by reference.

TECHNOLOGY FIELD

The present application relates generally to methods and systems for dynamically controlling flow through a heart-lung machine.

BACKGROUND

Heart-lung-machines (HLM) are used to perform the function of the heart and lungs during open heart and/or traditional surgeries. An HLM circulates oxygenated blood to the brain and other vital organs. An HLM may include a primary pump and one or more subordinate pumps which take some of the flow from the primary pump. If the flow of the master pump is reduced without correcting the flow of the subordinate pumps, blood flow to the aorta may be compromised. Improved flow control systems and methods may be desired.

SUMMARY

This disclosure provides methods and systems for dynamically controlling a flow through one or more subordinate pumps.

One illustrative example is a method for controlling one or more pumps of a heart-lung-machine. The method includes receiving an actual flow rate of a pump, determining the actual flow rate is from a primary pump, determining an available amount of the actual flow rate of the primary pump that is available to one or more subordinate pumps, comparing the available amount of the actual flow rate of the primary pump to a sum of set flow rates of the one or more subordinate pumps, and operating the one or more subordinate pumps in a proactive control mode or a reactive control mode.

Alternatively or in addition to any example herein, when the sum of set flow rates of the one or more subordinate pumps is less than the available amount of the actual flow rate of the primary pump the one or more subordinate pumps are operated in a proactive control mode.

Alternatively or in addition to any example herein, when in the proactive control mode, manual adjustment of a flow rate of the one or more subordinate pumps is limited to a predetermined maximum flow rate.

Alternatively or in addition to any example herein, the predetermined maximum flow rate is based on the difference in the available amount of the actual flow rate of the primary pump and the sum of set flow rates of the one or more subordinate pumps.

Alternatively or in addition to any example herein, the method includes transmitting a notification indicating the one or more subordinate pumps are operating in a proactive control mode.

Alternatively or in addition to any example herein, when the sum of set flow rates of the one or more subordinate pumps is greater than the available amount of the actual flow rate of the primary pump the one or more subordinate pumps are operated in a reactive control mode.

Alternatively or in addition to any example herein, when in the reactive control mode determining an incremental speed adjustment for the one or more subordinate pumps.

Alternatively or in addition to any example herein, the method includes applying the incremental speed adjustment to the one or more subordinate pumps to operate the one or more subordinate pumps at an intervention speed.

Alternatively or in addition to any example herein, the intervention speed reduces a flow rate of each of the subordinate pumps.

Alternatively or in addition to any example herein, the method includes setting a flow rate of the one or more subordinate pumps to zero if the available amount of the actual flow rate of the primary pump is less than a predetermined flow rate.

Another illustrative example is a heart-lung-machine (HLM) including a venous reservoir, an oxygenator, a primary pump having a primary flow and configured to pump blood from the venous reservoir, through the oxygenator, and into a patient, one or more subordinate pumps configured to supply blood to one or more components of the HLM and/or into the patient, a flow of the one or more subordinate pumps supplied via the primary flow, and one or more controllers each operably coupled to one of the one or more subordinate pumps. Each of the one or more controllers configured to receive a current actual flow rate of the primary pump, determine an available amount of the actual flow rate of the primary pump that is available to its coupled subordinate pump, compare the available amount of the actual flow rate of the primary pump to a sum of set flow rates of the one or more subordinate pumps, and operate its coupled subordinate pump in a proactive control mode or a reactive control mode.

Alternatively or in addition to any example herein, when the sum of set flow rates of the one or more subordinate pumps is less than the available amount of the actual flow rate of the primary pump the one or more subordinate pumps are operated in a proactive control mode, and when the sum of set flow rates of the one or more subordinate pumps is greater than the available amount of the actual flow rate of the primary pump the one or more subordinate pumps are operated in a reactive control mode.

Alternatively or in addition to any example herein, when in the proactive control mode, manual adjustment of a flow of the one or more subordinate pumps is limited to a predetermined maximum.

Alternatively or in addition to any example herein, when in the reactive control mode, each of the one or more controllers is further configured to determine an incremental reduction of a speed of its coupled subordinate pump.

Alternatively or in addition to any example herein, the incremental reduction of the speed is applied to an actual speed of the coupled subordinate pump to operate the coupled subordinate pump at a lower flow rate.

Alternatively or in addition to any example herein, each of the one or more controllers is configured to incrementally lower a flow rate of its coupled subordinate pump until the sum of set flow rates of the one or more subordinate pumps is less than the available amount of the actual flow rate of the primary pump.

Alternatively or in addition to any example herein, each of the one or more controllers is configured to operate its coupled subordinate pump in the reactive mode until the sum of set flow rates of the one or more subordinate pumps is less than the available amount of the actual flow rate of the primary pump.

Alternatively or in addition to any example herein, the incremental reduction of the speed of the coupled subordinate pump is unique to each subordinate pump of the one or more subordinate pumps.

Another illustrative example is a method for dynamically controlling one or more pumps of a heart-lung-machine (HLM). The method includes receiving an actual flow rate of a primary pump, determining an available amount of the actual flow rate of the primary pump that is available to one or more subordinate pumps, and comparing the available amount of the actual flow rate of the primary pump to a sum of set flow rates of the one or more subordinate pumps. When the sum of set flow rates of the one or more subordinate pumps is less than the available amount of the actual flow rate of the primary pump, the method includes operating the one or more subordinate pumps are operated in a proactive control mode. When the sum of set flow rates of the one or more subordinate pumps is greater than the available amount of the actual flow rate of the primary pump, the method includes operating the one or more subordinate pumps are operated in a reactive control mode.

Alternatively or in addition to any example herein, the method includes transmitting a notification to a display, the notification including one or more changes to control parameters of the HLM.

The above summary of some example embodiments is not intended to describe each disclosed embodiment or every implementation of the disclosure.

BRIEF DESCRIPTION OF THE DRAWINGS

Embodiments of the present disclosure may be more completely understood in consideration of the following detailed description of various embodiments in connection with the accompanying drawings, in which.

Figure 1:
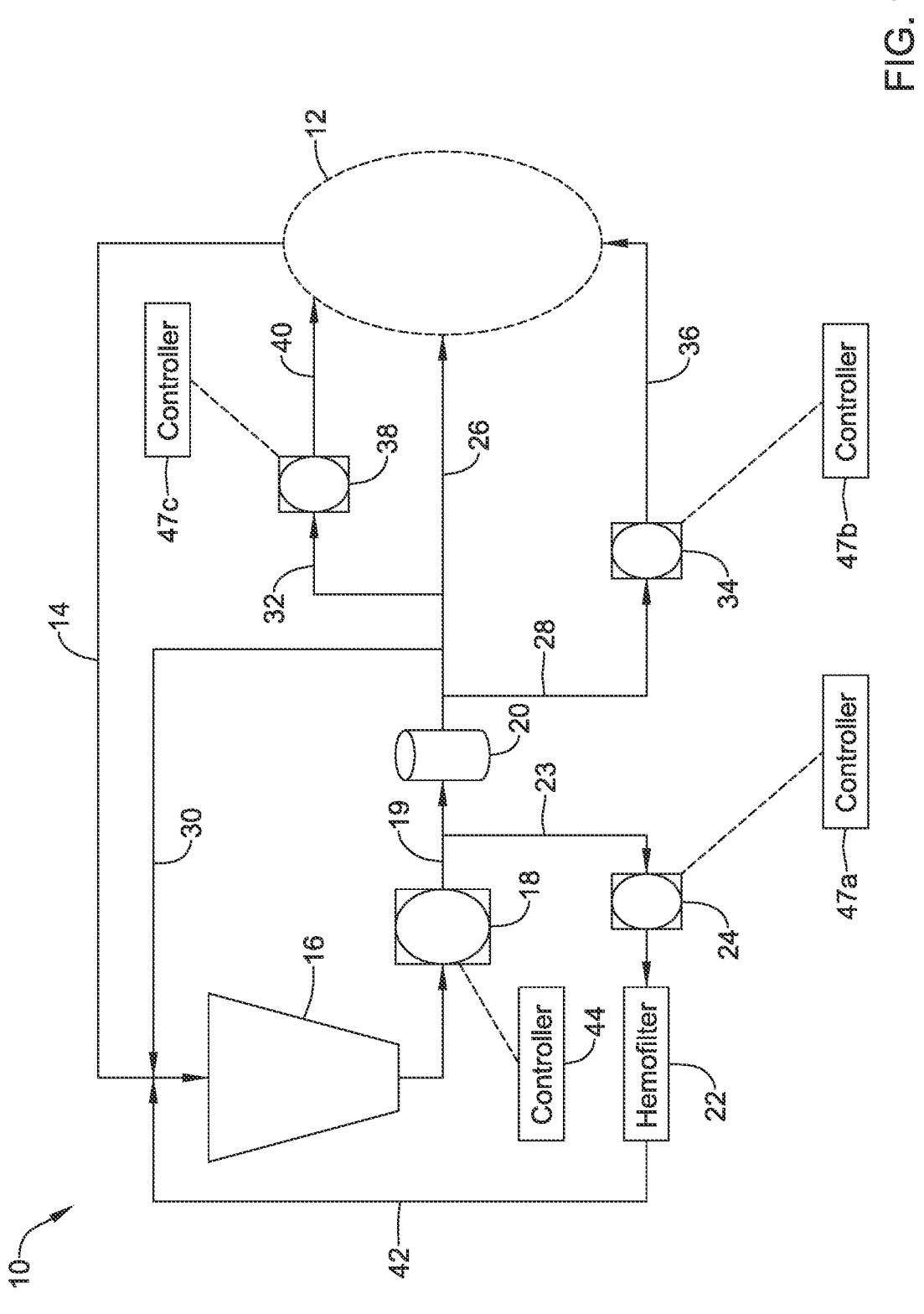
FIG. 1 is a schematic diagram of an illustrative heart-lung-machine.

While the embodiments of the present disclosure are amenable to various modifications and alternative forms, specifics thereof have been shown by way of example in the drawings and will be described in detail. It should be understood, however, that the intention is not to limit aspects of the present disclosure to the particular embodiments described. On the contrary, the intention is to cover all modifications, equivalents, and alternatives falling within the spirit and scope of the present disclosure.

DETAILED DESCRIPTION OF EXEMPLARY EMBODIMENTS

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

A cardiopulmonary bypass machine (CPM), or a heart-lung-machine (HLM) may be used to perform the function of the lungs and heart when the heart is stopped for a surgical procedure. Generally, an HLM may include a primary or master pump and one or more subordinate pumps which take some of the flow from the primary pump. If the flow of the master pump is reduced without adjusting the flow of one or more of the subordinate pumps, blood flow to the aorta may be reduced. In other cases, when one or more subordinate pumps are present, it may be possible for the subordinate pump(s) to utilize too much of the primary pump flow thus undesirably drawing blood flow from the aorta. Such a situation may be dangerous to the patient. For instance, air may be drawn through a leak in the blood line, caused by the underpressure originating from the reverse blood flow, or collapsing of the aorta or other arterial vessels due to the underpressure.

The present disclosure is directed towards an HLM and method of operation the HLM which dynamically controls multiple subordinate pumps so that their combined flow is kept lower than the flow of the supplying primary pump using one or more control algorithms. In some cases, one of the subordinate pumps may be controlled by a "keep lower" algorithm to automatically reduce the flow of the subordinate pump when the flow of the primary pump is reduced. In other cases, the speed of the primary pump may be automatically increased using a control algorithm when the user manually increases the flow of one or more subordinate pumps to ensure the flow rate of the supplying primary pump remains higher than the combined flow rates of the subordinate pump(s). In other words, the control algorithm may automatically increase the speed, and thus the flow, of the primary pump, in response to a user manually turning on or increasing the flow of one or more of a plurality of subordinate pumps of the HLM.

FIG. 1 is a schematic diagram of an illustrative heart-lung-machine (HLM) 10 and patient 12. Generally, a venous cannula 14 is inserted into the vena cava of the heart to direct blood flow from the patient 12 before it enters the heart to a venous reservoir 16. From the venous reservoir 16, the blood is pumped via an arterial or primary pump 18 to through a line 19 to an oxygenator 20. Some blood flow may be diverted through a side branch 23 to a hemofiltration system 22. In some cases, an additional pump 24 may be used to supply blood to the hemofiltration system 22. Blood may travel through a return 42 to the venous reservoir 16 after passing through the hemofiltration system 22. It is contemplated that the hemofiltration pump 24 can branch off the arterial pump 18 supply before or after the oxygenator 20.

While not explicitly shown, the blood may pass through a heat exchanger before or after entering the oxygenator 20. An arterial line 26 may take the oxygenated blood from the oxygenator 20 to the aorta of the patient 12. The arterial line 26 may include one or more branches 28, 30, 32 that take flow for delivery to locations in the body other than the aorta and/or to other components of the HLM 10. The branches 28, 30, 32 may take some of the flow in a passive or active manner. For example, a first branch 28 may be coupled to a pump 34, such as a cardioplegia pump, which actively takes blood flow from the arterial line 26 to be delivered to the patient 12 for Buckberg blood cardioplegia via a cardioplegia line 36. In some cases, the cardioplegia branch 28 can branch directly from an outlet of the oxygenator 20. A second branch 30 may passively return blood to the venous reservoir 16 via a shunt or other devices like a bubble trap. A third branch 32 may be coupled to a pump 38, such as a cerebral pump, which actively takes blood flow from the arterial line 26 to return to the patient 12 via a cerebral perfusion line 40. The branches 23, 28, 30, 32 after the oxygenator 20 can be positioned in any sequence and are not limited to the particular configuration illustrated in FIG. 1.

It is contemplated that the HLM 10 may include additional pumps, tubing, filtration, temperature control mechanisms, etc. beyond those illustrated in FIG. 1. It is further contemplated that some components illustrated in FIG. 1 may be omitted. Some illustrative HLM systems are described in commonly assigned PCT applicant publications WO 2020/125976, titled HEART LUNG MACHINE WITH CONTROL ASSEMBLY, WO 2020/259837, titled, DEVICE FOR AUTOMATICALLY ESTABLISHING THE VENOUS INFLOW TO A BLOOD RESERVOIR OF AN EXTRACORPOREAL BLOOD CIRCULATION SYSTEM, and WO 2020/126007, titled HEART-LUNG MACHINE WITH SIMPLIFIED SETUP BASED ON ROLE-PROFILE MAPPING, the disclosures of which are hereby incorporated by reference.

The HLM 10 may further include a controller 44 operatively coupled with the primary pump 18 and one or more controllers 47a, 47b, 47c (collectively, 47) each operatively coupled with the subordinate pumps 24, 34, 38. The controllers 44, 47 may be formed as an integral component of the pumps 18, 24, 34, 38 or as separate components from the pumps 18, 24, 34, 38. Alternatively, or additionally, the HLM 10 may include additional controllers. In some cases, the pumps 18, 24, 34 38 may be controlled by a common controller.

Figure 2:
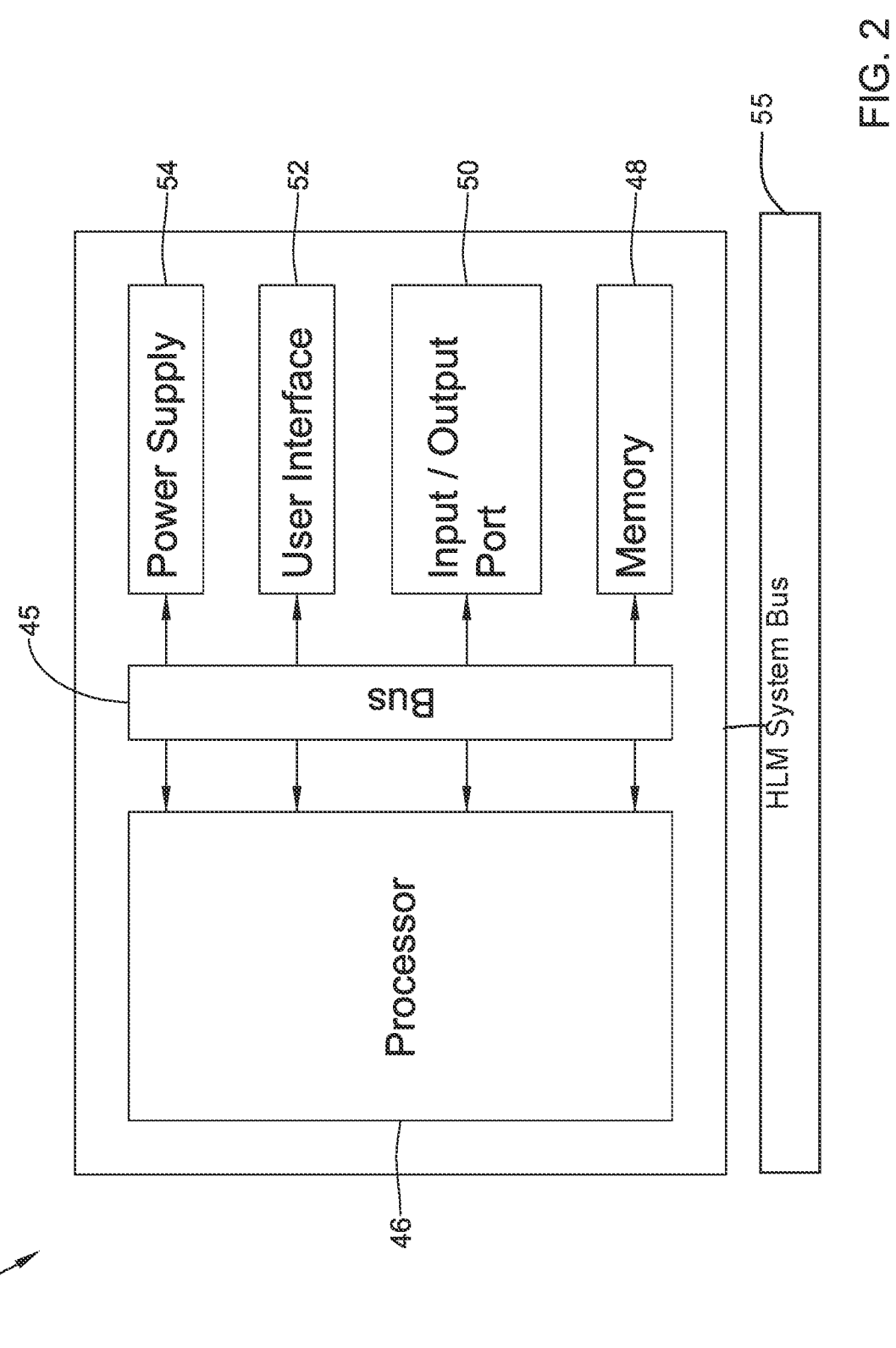
FIG. 2 is a schematic block diagram of an illustrative controller for controlling one or more components of a heart-lung-machine.

FIG. 2 is a schematic block diagram of an illustrative controller 44, 47. It is contemplated that the controller 44, 47 may be any computing device suitable for receiving inputs and providing outputs to the various components of the HLM. It is further contemplated that more than one controller may be provided. For example, the HLM 10 may utilize multiple controllers with decentralized control. In other examples, the HLM 10 may include a primary or supervisory controller and one or more subordinate controllers. Examples of computing devices include specialized computing devices or general-purpose computing devices such "control units," "control assemblies," "workstations," "servers," "hand-held devices," "heart lung machines," "controllers," and the like.

The controller 44, 47 may include a bus 45 that, directly and/or indirectly, couples the following devices: a processing unit 46, a memory 48, an input/output (I/O) port 50, a user interface 52, and a power supply 54. Any number of additional components, different components, and/or combinations of components may also be included in or connected to the computing device. For example, the controller 44, 47 may be connected to an HLM system bus 55 configured to transport control signals. The pumps 18, 24, 34, 38 may be connected to the HLM system bus 55 via pump-bus communication links. Similarly, the controllers 44, 47 may be operably coupled to the HLM system bus.

The memory 48 may be in communication with the processor 46. The memory 48 may be used to store any desired information such as, but not limited to, control algorithms, configuration protocols, set points, and the like. In some embodiments, the memory 48 may include specific control programs or modules configured to control the flow of the subordinate pumps 24, 34, 38 in response to the flow of the primary pump 18. The memory 48 may be any suitable type of storage device including, but not limited to, RAM, ROM, EPROM, flash memory, a hard drive, and/or the like. In some cases, the processor 46 may store information within the memory 48 and may subsequently retrieve the stored information from the memory 48. In embodiments, the memory 48 stores computer-executable instructions for causing the processor 46 to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

The input/output port (I/O port) 50 may have a number of wire terminals for receiving one or more signals from the pumps 18, 24, 34, 38 and/or system components and/or for providing one or more control signals to the pumps 18, 24, 34, 38 and/or system components. In some cases, the I/O port 50 may communicate with one or more components of the system 10, including, but not limited to, the pumps 18, 24, 34, 38. In other cases, the HLM system bus 55 may provide the communication link between the controllers 44, 47 and one or more components of the system 10, including, but not limited to, the pumps 18, 24, 34, 38. The controller 44, 47 may have any number of wire terminals for accepting a connection from one or more components of the system 10. However, how many wire terminals are utilized and which terminals are wired is dependent upon the particular configuration of the system 10. Different systems 10 having different components and/or types of components may have different wiring configurations. In some cases, the I/O port 50 may be configured to receive wireless signals from the pumps 18, 24, 34, 38 and/or one or more components or sensors (not explicitly shown). Alternatively, or additionally, the I/O port 50 may communicate with another controller.

The user interface 52 may include a display and a means for receiving user input (e.g., a microphone, a joystick, a satellite dish, a scanner, a printer, a wired and/or wireless device, a keyboard, a pen, a voice input device, a touch input device, a touch-screen device, an interactive display device, a mouse, and/or the like). In some cases, the user interface 52 may be integral to, or a part of, the controller 44, 47. Alternatively, or additionally, the controller 44, 47 may be operatively coupled to a remotely located user interface 52 including a display and a means for receiving user input. For example, the remotely located user interface 52 may be a separate display, a portable device, such as, but not limited to a smartphone, tablet computer, laptop computer, etc., or other such device. Additionally, or alternatively, the user interface 52 may further include other components configured to present information to a user such as, for example, a display device, a speaker, a printing device, and/or the like. In some cases, a user interface 52 may be omitted.

The bus 45 represents what may be one or more busses (such as, for example, an address bus, data bus, or combination thereof). Similarly, in embodiments, the controller 44, 47 may include a number of processing units 46, a number of memory components 48, a number of I/O ports 50, a number of user interface components 52, and/or a number of power supplies 54. Additionally, any number of these components, or combinations thereof, may be distributed and/or duplicated across a number of computing devices.

For the purposes of this disclosure, the pumps 24, 34, 38 which actively take flow from a line 19, 26 downstream of the arterial pump 18 and into a branch 23, 28, 32 are called subordinate pumps while the arterial pump 18 is called the primary pump. The primary pump 18 may provide all blood flow available to the subordinate pumps 24, 34, 38. However, as the primary pump 18 also delivers blood flow to the arterial line 26 directly to the patient, not all of the blood flow from the primary pump 18 is available to the subordinate pumps 24, 34, 38. Further, the flow rate of blood exiting the primary pump 18 may vary over the use of the HLM. It is contemplated that the flow rate of the primary pump 18 may be reduced for several different reasons. In one example, a user may manually reduce, slow, or stop the flow via one or more controls. In another example, the flow of the primary pump 18 may be reduced or stopped in response to a programmed control mechanism for overpressure control, in response to detection of air in a line, another safety parameter, or the like. However, if the flow of the primary pump 18 is reduced and the subordinate pumps 24, 34, 38 continue running at a same capacity as before the reduction, blood may be drawn from the aorta of the patient 12. This may be a harmful situation that could cause underpressure in the aortic cannula possibly followed by air intrusion. The same situation may occur if a subordinate pump 24, 34, 38 draws flow in reverse from a passive branch 30. It is contemplated that linking the control and flow of the subordinate pumps 24, 34, 38 to the control and flow of the primary pump 18 may prevent the subordinate pumps 24, 34, 38 from drawing more flow than the primary pump 18 is delivering.

In some cases, the controller 47 of each subordinate pump 24, 34, 38 may be configured to determine how much flow its respective subordinate pump 24, 34, 38 can take. The control mechanism will be described with respect to a single controller 47, however, it is contemplated that each controller 47a, 47b, 47c may be configured to determine how much flow the subordinate pump 24, 34, 38 it controls can take. In other examples, a single primary controller may be used to determine flow rates for each of the subordinate pumps 24, 34, 38. In other words, the controller 47 (either a single primary controller or separate controllers) of each subordinate pump 24, 34, 38 may be configured to monitor, sense and/or control the flow rate of the respective subordinate pump. When separate controllers 47a, 47b, 47c are provided at each subordinate pump 24, 34, 38, the controllers 47 may communicate with each other such that the flow through the other subordinate pumps 24, 34, 38 as well as the available flow from the primary pump 18 may be taken into consideration when determining a flow of a specific subordinate pump 24, 34, 38. The control algorithm may include entering a proactive control mode and a reactive control mode.

Generally, proactive control mode may occur when the set flow rate of an individual subordinate pump 24, 34, 38 is manually increased by means of a speed control knob (or other mechanical or computerized adjustment mechanism). As will be described in more detail herein, an individual controller 47 can use the information about the flow of the other subordinate pumps 24, 34, 38 and the flow of the primary pump 18 to determine how much flow is available to take. For example, each controller 47 may determine a maximum allowable flow rate based on the flow of the other subordinate pumps 24, 34, 38 and the flow of the primary pump 18. When the set flow rate of the individual subordinate pump 24, 34, 38 is increased by the user, the controller 47 of the individual subordinate pump 24, 34, 38 may restrict increases of actual flow when this available amount or predetermined maximum flow is reached. However, decreases in set flow rate of the subordinate pump by means of the control knob may be allowed, thus freeing the amount of available flow for other subordinate pumps 24, 34, 38. Feedback may be provided to the user to alert the user the flow of the subordinate pump 24, 34, 38 cannot be increased. Feedback may include alphanumeric textual message, beeps, lights, haptics, etc.

Generally, reactive control mode may occur when the flow of the primary pump 18 decreases (either by manual actuation of a control knob or by automated system reactions). Using the actual flow rates of each of the primary pump 18 and the subordinate pumps 24, 34, 38, a flow available to each of the subordinate pumps 24, 34, 38 can be calculated or determined. In some cases, the flow rate available to a particular subordinate pump 24, 34, 38 may be calculated as a percentage of the flow of primary pump 18. For example, the total flow rate available to the subordinate pumps 24, 34, 38 may be calculated as a percentage (e.g., 80%, 85%, 90%, or 95%) of the flow rate of the primary pump 18. Each subordinate pump 24, 34, 38, may in turn, be permitted to run at a set flow rate which is set as a percentage of the total flow rate of the primary pump 18, with the combined percentages of all the subordinate pumps 24, 34, 38 being less than or equal to 100%, or less than or equal to 90%, or instance, of the total flow rate of the primary pump 18. In other cases, the flow of a specific subordinate pump 24, 34, 38 may be calculated as a percentage of the total flow of all subordinate pumps 24, 34, 38. These percentages may be used to calculate or determine how much of the flow from the primary pump 18 is available to the specific subordinate pump 24, 34, 38. The flow to each specific subordinate pump 24, 34, 38 may then be automatically decreased using the control algorithm to the calculated or determined amount of flow that it can draw. This may prevent one pump from utilizing all of the flow from the primary pump 18 and leaving no flow or insufficient flow for the remaining pumps. Further, controlling the subordinate pumps such that the sum of the flow of subordinate pumps 24, 34, 38 is less than the flow from the primary pump 18 reduces the hazardous conditions noted above.

It is contemplated that the determination of the amount of flow available to each subordinate pump 24, 34, 38 may be performed by each controller 47 substantially simultaneously at a synchronized point in time. This may allow the subordinate pumps 24, 34, 38 to maintain their flow amount in relation to each other. As each subordinate pump 24, 34, 38 takes the difference between its actual (or current) flow and its calculated or determined available flow portion to control itself, the control mechanism is proportional control (proportional (P) controller characteristic). To allow for a smooth reaction, in some embodiments only a portion of the needed reduction is performed at one point in time. This may be achieved by a factor, Kp, which may be greater than zero and less than one, as will be described in more detail herein.

Figure 3:
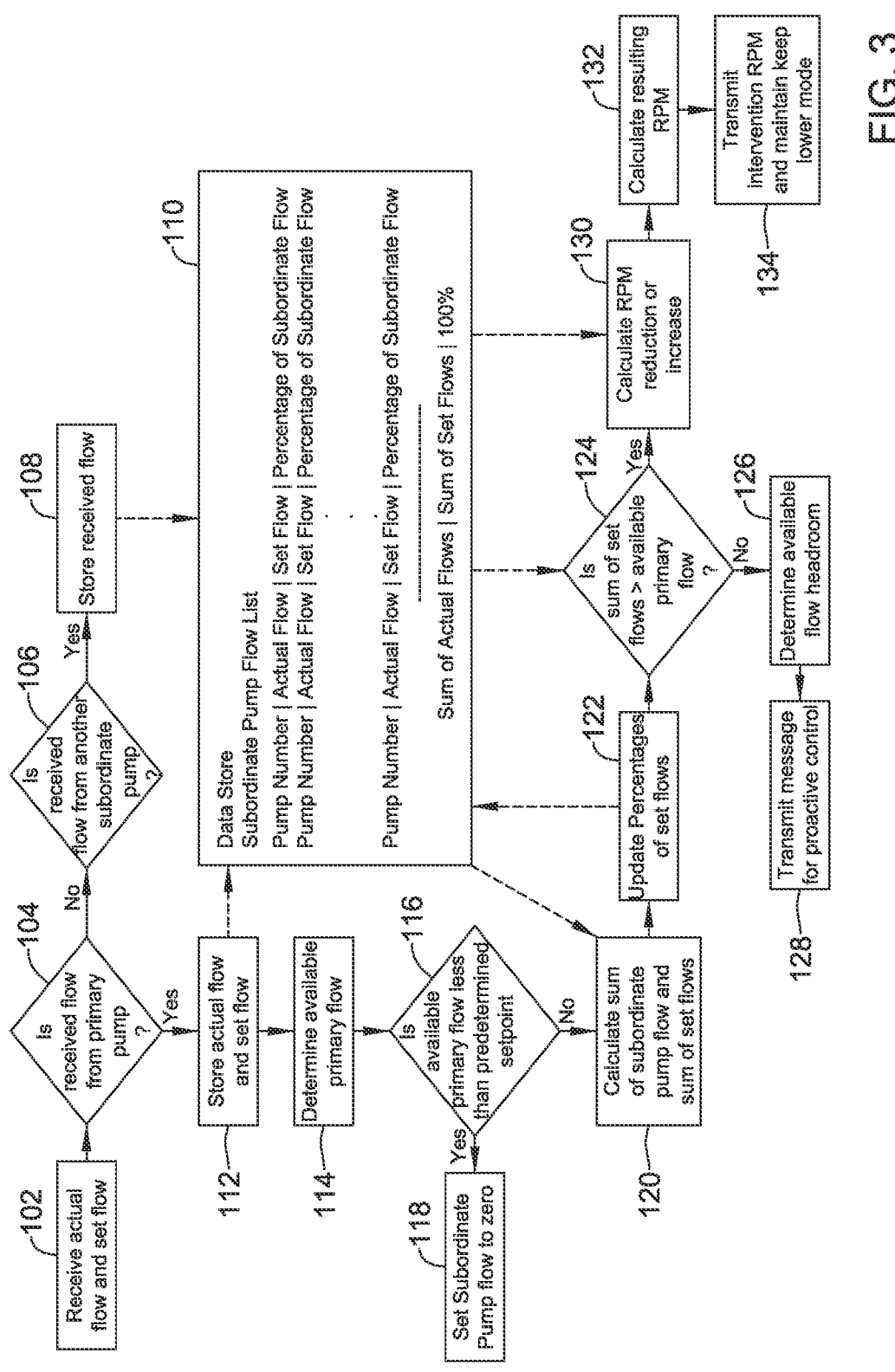
FIG. 3 is an illustrative control algorithm for controlling a flow rate of one or more subordinate pumps.

FIG. 3 is an illustrative flow chart of a control algorithm 100 that may be used to dynamically control one or more subordinate pumps 24, 34, 38. Generally, the control algorithm controls the subordinate pumps 24, 34, 38 so that the total flow rate of the combined subordinate pumps 24, 34, 38 is maintained lower than the flow rate of the supplying primary pump 18. The control algorithm 100 may be used for systems with fewer than three subordinate pumps or more than three subordinate pumps. The control algorithm 100 may be stored in a memory 48 of the controller 47 and executed by the processor 46 thereof. For clarity, the control algorithm 100 will be described with respect to the cardioplegia subordinate pump 34 and its corresponding controller 47b. However, it should be understood that the control algorithm 100 may be executed substantially simultaneously on other controllers 47a, 47c controlling subordinate pumps 24, 38. Further, in some cases, a single controller may be configured to perform the control algorithm 100 and issue control commands to each subordinate pump 24, 34, 38 in the HLM 10.

To begin, the controller 47b may receive a message 102 that includes an actual flow rate and/or a set flow rate from the primary pump 18 and/or the other subordinate pumps 24, 38. The actual flow rate is representative of a current flow rate of the pump while the set flow rate is a programmed flow rate. The actual flow rates and the set flow rates may be the same or different depending on the operating conditions of the HLM 10. In some cases, the controllers 44, 47 may be configured to broadcast the actual flow rate and the set flow rate for its respective pump 18, 24, 34, 38 at predetermined time intervals. Alternatively, or additionally, the controllers 44, 47 may be configured to broadcast the actual flow rate and the set flow rate for its respective pump 18, 24, 34, 38 in response to a change in a flow rate, or other control parameter. In some cases, the controller 47 may transmit the actual flow rate and the set flow rate for its respective pump 24, 34, 38 in response to receiving a flow rate from the primary pump 18. In yet other examples, the primary pump controller 44 may be configured to periodically transmit (e.g., at predetermined or random time intervals) the primary pump flow rate. This may trigger the subordinate pumps 24, 34, 38 to execute the control algorithm and/or to broadcast their respective actual and set flow rates. In other instances, the primary pump controller 44 may transmit the primary pump flow rate in response to receiving the flow rates of the subordinate pumps 24, 34, 38.

Once the controller 47b receives the message 102, the controller 47b may determine if the message was received from the primary pump 18, or primary pump controller 44, as shown at block 104. If the message 102 was not received from the primary pump 18, the controller 47b may then verify the message includes flow rates from another subordinate pump 24, 34, 38, as shown at block 106. The controller 47b may then store the received flow rates in a data store 110, as shown at block 108. In some cases, the data store 110 may be stored locally in the memory 48 of the controller 47b. Alternatively, or additionally, the data store 110 may be stored remotely from the controller 47b. When so provided, each controller 44, 47 may be communicatively coupled with a remote data store and each able to read/write to the remote data store.

The data store 110 may include a subordinate pump flow list which includes at least a pump name or number, the actual flow rate for said pump, the set flow rate for said pump, and a percentage of subordinate flow used by said pump. The set flow rate may be a set point calculated or determined by the controller or entered by the user via a user interface 52. In some cases, the actual flow rate of a subordinate pump 24, 34, 38 may be different from the set flow rate. The data store 110 may include this information for each subordinate pump 24, 34, 38 in the HLM 10. The sums of the subordinate flows of all subordinate pumps in the system may be first be calculated, as shown in Equations 1 and 2 below.

$$\text{SumofActualSubordinate Flows} = \Sigma\text{Actual SubordinateFlows} \qquad \text{Equation 1}$$

$$\text{SumofSetFlows} = \Sigma\text{SetSubordinateFlows} \qquad \text{Equation 2}$$

In some cases, the actual flow and the set flow for a same subordinate pump 24, 34, 38 may be different. The set flow of the subordinate pumps 24, 34, 38 is set by the user according to the medical need. For example, in some cases, the actual flow may be increased above the set flow when there is available headroom. In other examples, the actual flow may be reduced below the set flow to allow another pump to have an increased flow or to accommodate a reduced flow at the primary pump 18.

The sums of subordinate flows of all subordinate pumps in the system may then be used to determine the percentage of subordinate flow for a particular subordinate pump (e.g., $\text{Pump}_x$, $\text{Pump}_y$, $\text{Pump}_z$). In some cases, the percentage of subordinate flows may be calculated or determined using set flow rates, as shown in Equation 3 below. In other cases, the percentage of subordinate flows may be calculated or determined using actual flow rates, as shown in Equation 4 below.

$$\text{Equation 3}$$

$$\% \text{ of Subordinate } Flow_{Pump\,x} = \frac{\text{Set } Flow_{Pumpx}}{\text{Sum of set Flows of all Subordinate Pumps}} \times 100\%$$

$$\text{Equation 4}$$

$$\% \text{ of Subordinate } Flow_{Pump\,x} = \frac{\text{Actual } Flow_{Pumpx}}{\text{Sum of actual Flows of all Subordinate Pumps}} \times 100\%$$

The percent of subordinate flow may be calculated or determined for each subordinate pump. It is contemplated that using the actual flow rates (Equation 4) to determine the percentage of subordinate flows may allow for a different system behavior to be achieved. For example, a slow down or stopping of a subordinate pump 24, 34, 38 by pressure control, bubble alarm reaction, an open lid, or other condition would make flow budget available immediately for the other subordinate pumps as the percentage of subordinate flow of the slowed or stopped subordinate pump 24, 34, 38 would reduce. However, this may not allow the slowed or stopped subordinate pump 24, 34, 38 to gain this flow again automatically when the pressure control, bubble alarm, open lid, or other condition is resolved.

Returning to block 104, if the message is received from the primary pump 18, the controller 47*b* may update the data store 110 with the actual flow rate and/or the set flow rate of the primary pump 18, and/or with the actual flow rate of the subordinate pump 34 and/or the set flow rate of the subordinate pump 34, as shown at block 112. To compensate for tolerances of the flow of each pump 18, 24, 34, 38, the controller 47*b* may calculate or determine an available flow from the primary pump 18 as a fraction of the primary pump flow, as shown at block 114. In some cases, the controller 47*b* may utilize 90% as the fraction of the primary pump flow which is available. However, this is just an example, the controller 47*b* may be programmed to utilize any percentage less than 100%, as desired. The available primary flow rate utilizing 90% as an example fraction to account for tolerance is calculated as set forth in Equation 5 below.

$$AvailablePrimaryFlowRate = ReceivedPrimaryFlowRate \times 0.9 \qquad \text{Equation 5}$$

The controller 47*b* may then compare the available primary flow rate to a predetermined minimum flow rate required to operate the subordinate pump 34, as shown at block 116. If the available primary flow rate is less than the predetermined minimum flow rate, the controller 47*b* may set the flow rate of the subordinate pump 34 to zero, as shown at block 118, which may shut off the subordinate pump 34. For example, if the available primary flow rate is less than 0.1 liters per minute (1 pm), the controller 47*b* may set the flow rate of the subordinate pump 34 to zero. This is just one example. The predetermined minimum available primary flow rate may be less than 0.1 1 pm or greater than 0.1 1 pm, as desired. If the available primary flow rate is greater than the predetermined minimum, the controller 47*b* may calculate or update the sum of the actual flow rates of the subordinate pumps 24, 34, 38 (Equation 1) and the sum of the set flow rates of the subordinate pumps 24, 34, 38 (Equation 2), as shown at block 120. For example, as each controller 47 receives the primary flow rate from the primary pump 18 (block 104), each controller 47 updates the actual flow and set flow stored in the data store (block 112). The updated sums may be stored in the data store 110. The controller 47*b* may then calculate or update the percentage of subordinate flow used by one or more of the subordinate pumps 24, 34, 38 using Equation 3 or Equation 4, as shown at block 122. The updated percentages of subordinate flow may be stored in the data store 110.

The controller 47*b* may then compare the sum of the set flow rates of the subordinate pumps 24, 34, 38 to the available primary flow rate, as shown at block 124. If the sum of the set flow rates is not greater than the primary flow rate, the controller 47*b* operates the subordinate pump 34 using a proactive control mode. For example, when the primary flow rate is greater than the sum of the set flow rates of the subordinate pumps 24, 34, 38, there is flow available for the one or more of the subordinate pumps 24, 34, 38 to increase their respective flow rate. The controller 47*b* may then determine the available flow headroom (i.e., available flowrate) using Equation 6 below, as shown at block 126.

$$AvailableHeadroom = AvailablePrimaryFlow - Sumof ActualSubordinateFlows \qquad \text{Equation 6}$$

The controller 47*b* may then transmit a message or control command to the subordinate pump 34 to limit flow rate increases via the control knob (or other input), as shown at block 128. The message may include a maximum flow rate to which the subordinate pump 34 may be increased. The maximum flow rate may be based on an entirety of the available headroom or a fraction of the available headroom proportional to the percentage of subordinate flow for the particular pump. In some cases, the controller 47*b* may transmit a similar message to other subordinate pump controllers 47*a*, 47*c* and/or subordinate pumps 24, 34. In other cases, each subordinate pump controller 47 may be configured to calculate or determine flow rate limits and transmit said limits to its respective subordinate pump 24, 34, 38. The controller 47*b* may be configured transmit a message or notification to the user including the rate limit. In some cases, the notification may be presented via a display of the HLM 10 or to a user device. The notification may be a written alphanumeric message, a visual alert (e.g., a light), an audio alert (e.g., a beep or series of beeps), a haptic alert, etc. which is configured to relay to the user of the HLM 10 that a control change or a change in a control parameter has occurred or is in effect.

Returning to block 124, if the sum of the set flow rates is greater than the primary flow rate it may be necessary to reduce the flow rate of the subordinate pumps 24, 34, 38 and the controller 47*b* operates the subordinate pump 34 using a reactive control mode. To begin, the controller 47*b* may be configured to calculate or determine a speed or a revolution per minute (RPM) reduction or increase, as shown at block 130. This may be done using Equation 7 below.

$$RpmStep = \frac{\left( \begin{array}{c} AvailablePrimaryFlow - \\ SumofActualSubordinateFlows \end{array} \right) \times \\ \% \ ofSubordinateFlow_{Pumpx}}{FlowFactor_{Pumpx}} \times Kp \qquad \text{Equation 7}$$

It should be noted that the percent of subordinate flow and the flow factor are specific to the particular pump for which the speed (or RPM) change is being calculated. The flow factor may be determined by the mechanical geometry of the particular pump and by the diameter of the tube that is inserted in the pump, i.e., the diameter of the lumen of the tube that is inserted in the pump. As noted above Kp is a factor used in proportional control which may be greater than zero and less than one. The value for Kp may be experimentally derived. The Kp factor may be selected to balance a quick response to a needed flow reduction and a stable flow adjustment As can be seen from Equation 7 above, if the sum of the actual flow rates of the subordinate pumps is greater than the available primary flow rate, the RPM step of the subordinate pump will be negative. Thus, the speed (or RPM) and the flow rate of the subordinate pump 24, 34, 38 will be reduced.

The RPM step may be calculated or determined for each subordinate pump 24, 34, 38 such that each subordinate pump 24, 34, 38 reduces its flow by an amount proportional to its percent of total subordinate flow. Thus, the incremental speed reduction or RPM step may be unique or different for each subordinate pump 24, 34, 38. In this way, the needed flow reduction may be distributed over all the subordinate pumps 24, 34, 38. As noted above, the primary pump 18 or the primary pump controller 44 is configured to transmit the flow rate of the primary pump 18 substantially simultaneously to each subordinate pump 24, 34, 38 or controller 47 thereof. This synchronization of data transmission may allow all subordinate pumps 24, 34, 38 to perform the RPM step calculation the perform the necessary flow reduction nearly at the same point in time and report the result to the other subordinate pumps 24, 34, 38 during the time interval until the next sampling point. Once the RPM step is determined, the step should be added to the mean actual RPM of the respective subordinate pump 24, 34, 38, as shown at block 132 to determine an intervention RPM or speed, as shown in Equation 8.

$$\text{InterventionRpm=MeanRpm+RpmStep} \qquad \text{Equation 8}$$

The intervention RPM or speed determined by the controller 47b may be transmitted to the subordinate pump 34 and the other subordinate pumps, as shown at block 134, and the RPM of the subordinate pump 34 adjusted to the intervention RPM. For example, each subordinate pump 24, 34, 38 is capable of individually reducing the flow while the other subordinate pumps may get the flow in which the reduction results in. The subordinate pumps 24, 34, 38 may be maintained in a "keep lower" mode until the flow rate of the primary pump 18 is increased. Further, when the subordinate pumps 24, 34, 38 are in the keep lower mode, manual increases to the flow rate of the subordinate pumps 24, 34, 38 via a control knob or other input are not allowed or are locked out. The control algorithm 100 may be repeated each time the primary pump 18 or primary pump controller 44 transmits its current flow rate to the subordinate pumps 24, 34, 38. In some cases, the necessary flow reduction at the subordinate pumps 24, 34, 38 may occur over a number of iterative cycles of the control algorithm. In some cases, the controller 47b may be configured transmit a message or notification information the user of the current operating mode or conditions. In some cases, the notification may be presented via a display of the HLM 10 or to a user device. The notification may be a written alphanumeric message, a visual alert (e.g., a light), an audio alert (e.g., a beep or series of beeps), a haptic alert, etc. which is configured to relay to the user of the HLM 10 that a control change or a change in a control parameter has occurred or is in effect.

It should be understood that this disclosure is, in many respects, only illustrative. Changes may be made in details, particularly in matters of shape, size, and arrangement of steps without exceeding the scope of the present disclosure. This may include, to the extent that it is appropriate, the use of any of the features of one example embodiment being used in other embodiments. The scope of the present disclosure is, of course, defined in the language in which the appended claims are expressed.

What is claimed is:

1. A method of controlling one or more subordinate pumps of a heart lung machine dynamically using one or more controllers, the method comprising:

receiving, at the one or more controllers, a primary pump flow rate value corresponding to an actual flow rate outputted by a primary pump of the heart lung machine;

determining, by the one or more controllers, a determined available amount of the actual flow rate outputted by the primary pump available to the one or more subordinate pumps;

comparing, using the one or more controllers, the determined amount to a sum of set flow rates of the one or more subordinate pumps; and operating the one or more subordinate pumps dynamically using the one or more controllers a reactive control mode based on the comparing wherein the operating is in a reactive control mode when the sum of set flow rates is greater than the determined available amount and the reactive control mode comprises determining an incremental speed adjustment for at least one subordinate pump and reducing a flow rate of the at least one subordinate pump by applying the incremental speed adjustment; and wherein the operating is in a proactive control mode when the sum of set flow rates is less than the determined available amount and the proactive control mode comprises limiting a manual increase of a flow rate of at least one subordinate pump to a predetermined maximum flow rate value.

2. The method of claim 1, wherein the predetermined maximum flow rate is based on a difference in the available amount of the actual flow rate of the primary pump and the sum of set flow rates of the one or more subordinate pumps.

3. The method of claim 1, further comprising transmitting, when the operating is in the proactive control mode, a notification indicating the one or more subordinate pumps are operating in the proactive control mode.

4. The method of claim 1, wherein the receiving further comprises receiving flow data for each of the one more subordinate pumps.

5. The method of claim 1, further comprising setting a flow rate of the one or more subordinate pumps to zero when the available amount of the actual flow rate of the primary pump is less than a predetermined flow rate.

* * * * *